US010549831B2

(12) United States Patent
Salters et al.

(10) Patent No.: US 10,549,831 B2
(45) Date of Patent: Feb. 4, 2020

(54) DEVICE HAVING SURFACES AND AN ANTI-BIOFOULING SYSTEM COMPRISING AT LEAST ONE ANTI-BIOFOULING LIGHT SOURCE FOR EMITTING RAYS OF ANTI-BIOFOULING LIGHT

(71) Applicant: KONINKLIJKE PHILIPS N.V., Eindhoven (NL)

(72) Inventors: Bart Andre Salters, Eindhoven (NL); Roelant Boudewijn Hietbrink, Utrecht (NL)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 16/070,045

(22) PCT Filed: Jan. 20, 2017

(86) PCT No.: PCT/EP2017/051176
§ 371 (c)(1),
(2) Date: Jul. 13, 2018

(87) PCT Pub. No.: WO2017/125543
PCT Pub. Date: Jul. 27, 2017

(65) Prior Publication Data
US 2019/0016426 A1 Jan. 17, 2019

(30) Foreign Application Priority Data

Jan. 20, 2016 (EP) ..................................... 16151990
Aug. 17, 2016 (EP) ..................................... 16184438

(51) Int. Cl.
*B63H 5/16* (2006.01)
*A61L 2/08* (2006.01)
(Continued)

(52) U.S. Cl.
CPC .................. *B63H 5/16* (2013.01); *A61L 2/08* (2013.01); *A61L 2/10* (2013.01); *B08B 7/0035* (2013.01);
(Continued)

(58) Field of Classification Search
CPC . A61L 2/00; A61L 2/10; A61L 2/0011; B08B 7/00; B08B 7/0057; B08B 17/02; B63B 59/08; C02F 1/32; C02F 1/325
(Continued)

(56) References Cited

U.S. PATENT DOCUMENTS 5,308,505 A * 5/1994 Titus ..................... A61L 2/0011
210/745
5,322,569 A 6/1994 Titus et al.
(Continued)

FOREIGN PATENT DOCUMENTS

EP 1742835 B1 1/2012
GB 1462815 A 1/1977
(Continued)

*Primary Examiner* — Lars A Olson

(57) ABSTRACT

A device (100) has surfaces (21, 22, 23, 24) and an anti-biofouling system (10) comprising at least one light source (11, 12) for performing an anti-biofouling action on at least a majority of the surfaces, the at least one light source (11, 12) being adapted to emit rays of anti-biofouling light. The surfaces (21, 22, 23, 24) are configured relative to each other and to the at least one light source (11, 12) such that during operation of the at least one light source, at least a majority of the surfaces (21, 22, 23, 24) is free from shadow with respect to the rays of anti-biofouling light from the at least one light source (11, 12), wherein it may be possible for the rays of anti-biofouling light to reach the surfaces (21, 22, 23, 24) by skimming along the surfaces (21, 22, 23, 24).

10 Claims, 8 Drawing Sheets

(51) Int. Cl.
*A61L 2/10* (2006.01)
*C02F 1/32* (2006.01)
*B08B 7/00* (2006.01)
*B08B 17/02* (2006.01)
*F28F 19/00* (2006.01)
*B63B 9/00* (2006.01)
*B63H 20/12* (2006.01)
*F28F 3/08* (2006.01)

(52) U.S. Cl.
CPC ............... *B08B 17/02* (2013.01); *B63B 9/00* (2013.01); *B63H 20/12* (2013.01); *C02F 1/32* (2013.01); *F28F 3/08* (2013.01); *F28F 19/00* (2013.01); *F28F 2265/20* (2013.01)

(58) Field of Classification Search
USPC .................................................. 440/53; 134/1
See application file for complete search history.

(56) References Cited

U.S. PATENT DOCUMENTS

| 6,267,924 | B1 | 7/2001 | Fencl et al. |
| 2007/0080081 | A1 | 4/2007 | Chang |
| 2012/0050520 | A1* | 3/2012 | Thoren ................. B63B 59/08 348/81 |
| 2018/0001356 | A1* | 1/2018 | Salters ................. B08B 7/0057 |

FOREIGN PATENT DOCUMENTS

| KR | 2015137404 A | 12/2015 |
| RU | 2170216 C1 | 7/2001 |
| WO | 2011078771 A1 | 6/2011 |
| WO | 2013032599 A1 | 3/2013 |
| WO | 2014014779 A1 | 1/2014 |

* cited by examiner

DEVICE HAVING SURFACES AND AN ANTI-BIOFOULING SYSTEM COMPRISING AT LEAST ONE ANTI-BIOFOULING LIGHT SOURCE FOR EMITTING RAYS OF ANTI-BIOFOULING LIGHT

CROSS-REFERENCE TO PRIOR APPLICATIONS

This application is the U.S. National Phase application under 35 U.S.C. § 371 of International Application No. PCT/EP2017/051176, filed on 20 Jan. 2017, which claims the benefit of European Patent Application No. 16151990.5, filed on 20 Jan. 2016 and European Patent Application No. 16184438.6, filed on 17 Aug. 2016. These applications are hereby incorporated by reference herein.

FIELD OF THE INVENTION

The invention relates to a device having surfaces and an anti-biofouling system comprising at least one anti-biofouling light source for performing an anti-biofouling action on at least a majority of the surfaces, the at least one anti-biofouling light source being adapted to emit rays of anti-biofouling light.

BACKGROUND OF THE INVENTION

In practice, many examples of a device having surfaces to be kept clean from biofouling exist, including devices intended for use in a domestic context, such as coffee makers, water disinfectors and boilers, and also including devices intended for use in an industrial context or a marine context, such as box coolers. In general, biofouling of surfaces is a well-known problem, which particularly occurs in the context of surfaces which are exposed, at least during a part of their entire lifetime period, to water or another fluid in which biofouling organisms are present.

Biofouling or biological fouling is the accumulation of microorganisms, plants, algae, small animals and the like on surfaces. According to some estimates, over 1,700 species comprising over 4,000 organisms are responsible for biofouling. Hence, biofouling is caused by a wide variety of organisms. Biofouling is divided into micro biofouling which includes biofilm formation and bacterial adhesion, and macro biofouling which includes the attachment of larger organisms. Due to the distinct chemistry and biology that determine what prevents them from settling, organisms are also classified as being hard or soft. Hard biofouling organisms include calcareous organisms such as barnacles, encrusting bryozoans, mollusks, polychaetes and other tube worms, and zebra mussels. Soft biofouling organisms include non-calcareous organisms such as seaweed, hydroids, algae and biofilm "slime". Together, these organisms form a biofouling community.

In several situations, biofouling creates substantial problems. Biofouling can cause machinery to stop working, water inlets to get clogged, and heat exchangers to suffer from reduced performance. Hence, the topic of anti-biofouling, i.e. the process of removing or preventing biofouling, is well-known. In industrial processes involving wetted surfaces, bio dispersants can be used to control biofouling. In less controlled environments, biofouling organisms are killed or repelled with coatings using biocides, thermal treatments or pulses of energy. Nontoxic mechanical strategies that prevent organisms from attaching to a surface include choosing a material or coating for causing the surface to be slippery, or creating nanoscale surface topologies similar to the skin of sharks and dolphins which only offer poor anchor points.

Box coolers are heat exchangers comprising a plurality of pipes extending at quite a close distance with respect to each other, which are especially intended for use in engine-driven marine vessels such as ships. Normally, a ship is equipped with various kinds of machinery, and one or more box coolers of which at least the pipes are arranged in one or more sea chests may be used in a machinery cooling system of the ship. The pipes of a box cooler serve for containing and transporting fluid to be cooled in their interior, wherein it is a practical option for a sea chest accommodating the pipes to have both inlet openings and outlet openings so that water can enter the sea chest, flow over the pipes in the sea chest, and exit the sea chest through natural flow and/or under the influence of motion of the ship. Biofouling of a box cooler is a major problem in view of the fact that layers of biofouling are effective heat insulators, so that biofouling involves a decrease of the heat transferring capability of the box cooler. When the biofouling layers are so thick that seawater can no longer circulate between adjacent pipes of the box cooler, an additional deteriorating effect on the heat transfer is obtained. Thus, biofouling of box coolers increases the risk of engine over-heating, so that ships need to slow down or damage of ship engines occur.

For example, in the case of a tugboat having an installed engine power of 15 MW, one or more box coolers are applied for transferring heat in the order of 5 MW to the seawater. Usually, a box cooler comprises bundles of U-shaped pipes for conducting a fluid to be cooled, wherein ends of leg portions of the pipes are secured to a common plate having openings for providing access to both leg portions of each of the pipes. It is a very practical option to enable the box cooler to perform its cooling function by continuously exposing the pipes thereof to fresh seawater, as mentioned in the foregoing. However, the environment of a box cooler is ideally suited for biofouling, as the seawater is heated to a medium temperature in the vicinity of the pipes as a result of the heat exchange with the relatively hot fluid in the interior of the pipes during operation of the box cooler, and the constant flow of water continuously brings in new nutrients and organisms which are known to cause biofouling.

Anti-biofouling arrangements for cooling units that cool the water from a cooling water system of an engine-driven ship by means of seawater are known in the art. For example, DE 102008029464 relates to a box cooler for use in ships and on offshore platforms, comprising an integrated anti-biofouling system for killing biofouling organisms by means of an overheating process that can be regularly repeated. In particular, the box cooler is protected against microorganism biofouling by continuously overheating a defined number of heat exchanger pipes without interrupting the cooling process, wherein waste heat from the cooling water may be used for doing so.

Plate coolers are heat exchangers comprising plates in a successive arrangement, and are typically used for enabling a transfer of heat between two liquids. The plates are normally made of metal or another material which is known for having high thermal conductivity. In a plate cooler, the liquids are spread out over plates, so that it is possible to have a relatively large heat exchanger area and still have a compact overall construction. A widespread application of plate coolers is an application in combination boilers, for example, which does not alter the fact that application of plate coolers in an industrial context is also common. As the plates of a plate cooler are exposed to liquids throughout the lifetime of the plate cooler, biofouling of the plates occurs, which involves a reduction of the heat transferring capability of the plate coolers, and which may eventually lead to failure of the plate coolers, hindering the necessary flows of liquid through the plate coolers to a too high extent. This problem is all the more apparent when the plates are corrugated, which is often the case in practice, as having such plates is a way of realizing a further enlargement of the heat exchanger area. In the art, methods of cleaning plate coolers are known in order to alleviate the problems caused by the biofouling phenomenon, which methods include taking the plate coolers apart and cleaning the plates one by one.

In general, it is known in the art to use ultraviolet light for removing/preventing the formation of biofilm on wet surfaces. For example, WO 2014/014779 discloses a system for reducing fouling of a surface of an optically transparent element subjected to a marine environment, including a LED for emitting ultraviolet radiation, a mount for directing emitted ultraviolet radiation toward the optically transparent element, and control circuitry for driving the LED.

The invention is particularly relevant in respect of devices having surfaces which need to be kept clean from biofouling yet are not transparent to the rays of anti-biofouling light emitted by the anti-biofouling system during operation of the at least one anti-biofouling light source thereof. A problem associated with many conventional assemblies of a device having surfaces and an anti-biofouling system comprising at least one anti-biofouling light source for emitting rays of anti-biofouling light is that one or more of the surfaces are in the shadow with respect to the rays of anti-biofouling light from the at least one anti-biofouling light source, so that biofouling still occurs at those surfaces. This problem is especially apparent in case the device has many surfaces in a complex arrangement. For example, in the context of a conventional box cooler having an anti-biofouling system which comprises at least one anti-biofouling light source for emitting rays of ultraviolet light, it appears to be practically impossible to have the anti-biofouling effect as desired on the entire exterior surface of all pipes, because in a normal situation in which only a limited number of anti-biofouling light sources can be added to the box cooler, it cannot be avoided that pipes are in the way between other pipes and the one or more anti-biofouling light sources. Even if one or more anti-biofouling light sources are arranged at a position between pipes of the box cooler, no more than a possibility of increasing a total area of the surfaces to be kept clean from biofouling is realized, while the fact remains that it is not possible to have a situation in which the entire area of the surfaces can be reached by the rays of ultraviolet light.

SUMMARY OF THE INVENTION

It is an object of the invention to provide an actual possibility of keeping at least a majority of surfaces of a device clean from biofouling, probably keeping all of the surfaces of a device entirely clean from biofouling, without necessarily involving an increase in the amount of anti-biofouling light sources for emitting rays of anti-biofouling light and/or a need to incorporate the anti-biofouling light sources in the surfaces. According to the invention, a device having surfaces and an anti-biofouling system is provided, the anti-biofouling system comprising at least one anti-biofouling light source for performing an anti-biofouling action on at least a majority of the surfaces, the at least one anti-biofouling light source being adapted to emit rays of anti-biofouling light, wherein the surfaces are configured relative to each other and to the at least one anti-biofouling light source such that during operation of the at least one anti-biofouling light source, at least a majority of the surfaces is free from shadow with respect to the rays of anti-biofouling light from the at least one anti-biofouling light source.

The invention provides a way of realizing total or near-total anti-biofouling coverage of the surfaces of a device, which surfaces are to be subjected to an anti-biofouling action. To this end, the invention involves an adjustment of the configuration of the surfaces of the device, particularly an adjustment of the configuration of the surfaces relative to each other and to the at least one anti-biofouling light source, which involves an adjustment of the arrangement/positioning and/or the design/shape of the surfaces, wherein the adjustment is done in such a way that it is possible to let at least a majority of the surfaces be under the influence of at least one anti-biofouling light source of the anti-biofouling system, and to avoid as much as possible a situation in which areas of one or more surfaces are in the shadow with respect to the rays of anti-biofouling light from the at least one anti-biofouling light source. As mentioned in the foregoing, examples of the device according to the invention include plate coolers and box coolers, and a feasible example of the anti-biofouling system which is part of the device according to the invention is an anti-biofouling system relying on the use of ultraviolet light, which does not alter the fact that many more examples of both the device and the anti-biofouling system which is part of the device are possible within the framework of the invention.

For the sake of completeness, the following is noted in respect of anti-biofouling by using ultraviolet light. An anti-biofouling light source may be chosen to specifically emit ultraviolet light of the c type, which is also known as UVC light, and even more specifically, light with a wavelength roughly between 250 nm and 300 nm. It has been found that most biofouling organisms are killed, rendered inactive, or rendered unable to reproduce by exposing them to a certain dose of the ultraviolet light. A typical intensity which appears to be suitable for realizing anti-biofouling is 10 mW per square meter, to be applied continuously or at a suitable frequency. A very efficient source for producing UVC light is a low pressure mercury discharge lamp, in which an average of 35% of input power is converted to UVC power. Another useful type of lamp is a medium pressure mercury discharge lamp. The lamp may be equipped with an envelope of special glass for filtering out ozone-forming radiation. Furthermore, a dimmer may be used with the lamp if so desired. Other types of useful UVC lamps are dielectric barrier discharge lamps, which are known for providing very powerful ultraviolet light at various wavelengths and at high electrical-to-optical power efficiencies, and LEDs. In respect of the LEDs, it is noted that they can generally be included in relatively small packages and consume less power than other types of light sources. LEDs can be manufactured to emit (ultraviolet) light of various desired wavelengths, and their operating parameters, most notably the output power, can be controlled to a high degree.

A light source for emitting ultraviolet light can be provided in the form of an elongated tubular lamp, more or less comparable to a well-known TL (tube luminescent/fluorescent) lamp. For various known germicidal tubular UVC lamps, the electrical and mechanical properties are comparable to those properties of tubular lamps for producing visible light. This allows the UVC lamps to be operated in the same way as the well-known lamps, wherein an electronic or magnetic ballast/starter circuit may be used, for example.

An advantage of using ultraviolet light for realizing anti-biofouling is that the microorganisms are prevented from adhering and rooting on the surface to be kept clean. Prevention of biofouling is generally preferred over removal of biofouling, as the latter requires more input power and involves a higher risk that an anti-biofouling action is not sufficiently effective.

According to an insight underlying the invention, an anti-biofouling action of rays of anti-biofouling light on a surface cannot only be realized by letting the rays impact on the surface at a certain angle with respect to the surface, but can also be realized when the rays of anti-biofouling light are made to skim along the surface. Hence, in particular applications of the invention, it may be so that at least one of the surfaces of the device is configured for allowing rays of anti-biofouling light emitted by the anti-biofouling system during operation of the at least one anti-biofouling light source thereof to skim along the surface, wherein it may even be so that the at least one of the surfaces of the device is in a position of exclusively being subjected to an anti-biofouling action by the skimming rays of anti-biofouling light. For example, at least one of the surfaces of the device is a planar surface which is oriented substantially parallel to and arranged alongside of a plane of rays of anti-biofouling light emitted by the anti-biofouling system during operation of the at least one anti-biofouling light source thereof, wherein optionally the planar surface is in a position of exclusively being subjected to an anti-biofouling action by the plane of rays of anti-biofouling light. In any case, in the context of the invention, it is found that rays of anti-biofouling light skimming along a surface are capable of effectively killing, rendering inactive or rendering unable to reproduce organisms on the surface which are otherwise prone to cause biofouling of the surface. This finding offers practical possibilities when it comes to configuring the surfaces to be subjected to an anti-biofouling action in such a way that none or only a minority of the surfaces is in the shadow with respect to the rays of anti-biofouling light from the at least one anti-biofouling light source of a given anti-biofouling system. In particular, the configuring process may be characterized by determining an orientation of surfaces in relation to features of the anti-biofouling system, especially a positioning of the at least one anti-biofouling light source of the anti-biofouling system, wherein the orientation of the surfaces is chosen such as to realize a situation in which rays of anti-biofouling light emitted by the anti-biofouling system during operation of the at least one anti-biofouling light source thereof are allowed to perform an anti-biofouling action on the surface by skimming along the surface. Including the skimming option as explained in the foregoing especially offers a possibility of having elements which are arranged one after another with respect to an anti-biofouling light source of the anti-biofouling system, in a row of which only a front element faces the anti-biofouling light source, and still subject side surfaces of the elements to an anti-biofouling action as required, for example by letting successive side surfaces extend in one and the same plane.

In a general sense, the anti-biofouling system which is part of the device according to the invention may comprise at least two anti-biofouling light sources. Also, in a general sense, the device according to the invention may comprise at least one functional element, the at least one functional element comprising at least one surface to be subjected to an anti-biofouling action. In practice, in order to guarantee that the at least one surface is free from shadow with respect to the rays of anti-biofouling light from the at least one anti-biofouling light source, it is advantageous for the at least one surface of the functional element to be provided with a planar or a concave shape, as opposed to a convex shape which is disadvantageous when it comes to allowing rays of anti-biofouling light coming from a certain direction to reach all of the surface or at least a major portion thereof.

It is very well possible for the device to comprise a number of functional elements, for example, functional elements which are adapted to direct a fluid for exchanging heat with the elements' surroundings. In that case, the functional elements may comprise pipes having a polygonal cross-section, or may comprise a number of interconnected units in successive arrangement, the units having an interior space, at least one inlet for supplying fluid to the interior space, and at least one outlet for discharging fluid from the interior space. The pipes as mentioned may be part of a box cooler, and the units as mentioned may be part of a plate cooler.

In respect of the case in which the functional elements comprise pipes having a polygonal cross-section, it is noted that it is advantageous for the pipes to comprise four flat side walls which are interconnected so as to surround an interior space of the pipes, in which case the cross-section of the pipes has four corners. In particular, in case the anti-biofouling system comprises elongated anti-biofouling light sources extending perpendicular to the pipes, it is a feasible option for the pipes to have a rectangular cross-section. The fact is that in that case, the pipes may be provided in a regular arrangement of adjacent rows, in such a way that only two elongated anti-biofouling light sources are needed for providing all of the exterior surfaces of the pipes with anti-biofouling light in a skimming fashion. Thus, when the invention is applied in the context of box coolers, it is found that it is advantageous to deviate from the common design according to which the pipes have a round/circular cross-section, as by providing pipes having a non-round/non-circular cross-section, it is possible to have total coverage of a total surface area of the box coolers to be kept clean from biofouling. In a general sense, when the functional elements have a polygonal cross-section, particularly a polygonal cross-section having a number of planar and/or concave sides, it may suffice to have a number of anti-biofouling light sources which is exactly two times lower than the number of sides of the functional elements.

Alternatively, it may be so that the anti-biofouling system comprises elongated anti-biofouling light sources extending parallel to the pipes, planar exterior surfaces of the pipes being oriented along an imaginary plane including a longitudinal axis of one of the anti-biofouling light sources. In such an orientation of the planar exterior surfaces of the pipes, it is ensured that rays of anti-biofouling light emitted by the anti-biofouling light source during operation thereof are capable of subjecting the surfaces to an anti-biofouling action by skimming along those surfaces. In the configuration of the pipes and the anti-biofouling light sources as mentioned, it is possible for the functional elements to further comprise plates being attached to the pipes and extending transversely to the pipes. Surfaces of such plates are subjected to an anti-biofouling action by skimming rays of anti-biofouling light, assuming that those surfaces are oriented so as to extend substantially perpendicular to the at least one elongated anti-biofouling light source, which furthermore involves the advantage that the presence of the plates does not prohibit complete coverage of the exterior surfaces of the pipes by the anti-biofouling system. The use of the plates as mentioned with the pipes is advantageous in view of the fact that the plates can act to enlarge the heat exchanger area.

In a practical embodiment, the device according to the invention comprises an enclosure for accommodating the at least one anti-biofouling light source of the anti-biofouling system, and for furthermore accommodating a fluid and/or at least one element, the surfaces of the device to be subjected to an anti-biofouling action including an interior surface of the enclosure. Hence, the interior surface of the enclosure also meets the requirement of being configured in such a way that the anti-biofouling system is allowed to act on that surface during operation of the at least one anti-biofouling light source thereof, with no more than only a minor portion of the surface being in the shadow with respect to the rays of anti-biofouling light from the at least one anti-biofouling light source, or even with the entire surface being covered by the anti-biofouling system. The enclosure may have one or more of various functions, including the function of shielding the environment of the device from the anti-biofouling light emitted by the anti-biofouling system during operation of the at least one anti-biofouling light source thereof, which is relevant in case the anti-biofouling light is ultraviolet light, which is a feasible possibility within the framework of the invention, as mentioned earlier. It is noted that in case the device comprises at least one functional element as mentioned earlier, the enclosure may serve for accommodating the at least one functional element and the at least one anti-biofouling light source of the anti-biofouling system.

In many practical embodiments of the device according to the invention, it may suffice to only have a maximum of two anti-biofouling light sources in the anti-biofouling system. This is especially true when the anti-biofouling light sources have an elongated appearance, which is a feasible option, as mentioned in the foregoing. Thus, when the surfaces of the device are configured in such a way that the surfaces are in a position of facing at least one anti-biofouling light source of the anti-biofouling system and/or a position of being under the influence of rays of anti-biofouling light acting on the surfaces by skimming along the surfaces during operation of the at least one anti-biofouling light source, with none or only a minority of the surfaces being in the shadow with respect to the rays of anti-biofouling light from the at least one anti-biofouling light source, it may be sufficient to have only a minimum of anti-biofouling light sources, which is a notable achievement of the invention.

In case the anti-biofouling system comprises two anti-biofouling light sources, and the device comprises surfaces which are blocked from directly facing either one of the anti-biofouling light sources, it may be so that such surfaces are oriented substantially parallel to and arranged alongside of a plane of rays of anti-biofouling light emitted by at least one of the anti-biofouling light sources. On the basis of the above explanation of aspects of the invention, it will be understood that with such an orientation of the surfaces, it is achieved that the surfaces may be subjected to an anti-biofouling action after all, as with such an orientation of the surfaces, it is achieved that rays of anti-biofouling light are allowed to act on the surfaces in a skimming fashion.

In respect of the case in which the functional elements comprise a number of interconnected units in successive arrangement, it is noted that it is advantageous for the at least one anti-biofouling light source of the anti-biofouling system to extend through the units, wherein it is practical for the anti-biofouling light source to have an elongated appearance. The units may be part of a heat exchanger system which comprises corrugated sheets for delimiting the units, which is of a type having an enlarged heat exchanger area when compared to a heat exchanger system of a type which comprises planar sheets. In order to prevent the corrugations of the sheets from being in the way between any portion of the sheets and the at least one anti-biofouling light source of the anti-biofouling system, the invention involves an orientation of the corrugations in which they extend in a straight direction along an imaginary plane including a longitudinal axis of an anti-biofouling light source of the anti-biofouling system. In conformity with explanations of the invention as provided in the foregoing, it is noted that with such an orientation of the corrugations, it is achieved that rays of anti-biofouling light emitted by the anti-biofouling system during operation of the at least one anti-biofouling light source thereof are allowed to skim along the corrugations, so that the surface of the sheets can be entirely covered by the anti-biofouling system.

According to one practical option, the respective units of the heat exchanger system are arranged at a distance with respect to each other. This option is especially applicable when the units are intended to be arranged in an enclosure which is suitable for containing a fluid which is capable of exchanging heat with fluid to be contained by the units, by flowing freely around and between the units. According to another practical option, which is known from the field of plate coolers, it may be so that a heat exchanger system comprises two groups of interconnected units in successive arrangement, wherein the units of the one group alternate with the units of the other group so as to have an optimal heat exchanging effect.

It follows from the foregoing that the invention relates to a device having surfaces to be subjected to an anti-biofouling action and an anti-biofouling system comprising at least one anti-biofouling light source for emitting rays of anti-biofouling light, wherein the surfaces of the device are configured so as to realize an arrangement of surfaces which is free or nearly free from shadow with respect to the rays of anti-biofouling light from the at least one anti-biofouling light source. In practice, the features of the invention may be realized when the majority of the surfaces has a normal which is at an angle of at most 90° towards at least one anti-biofouling light source, at any area of the surfaces, so that rays of anti-biofouling light emitted by the anti-biofouling system during operation of the at least one anti-biofouling light source thereof are allowed to reach the surfaces by impacting on the surfaces at a certain angle and/or skimming along the surfaces.

According to a feasible example existing within the framework of the invention, the device may be a boat drive and steer assembly, comprising a rotatable propeller and a fin extending downwardly from a propeller shaft casing which serves for accommodating a shaft of the propeller and associated gearing. In such a case, the anti-biofouling system may comprise at least one anti-biofouling light source which is arranged in the boat drive and steer assembly at a position for realizing total coverage or near-total coverage of the surface of the propeller as the propeller rotates. In respect of the propeller shaft, it is noted that this component of the boat drive and steer assembly may be hollow, in which case it is advantageous if material that is transparent to anti-biofouling light is applied in the propeller shaft, and if the anti-biofouling system comprises an elongated light source which is arranged so as to extend through the hollow propeller shaft. In such a configuration, the light source is well protected inside the propeller shaft, and in case the light source needs to be replaced, it is relatively easy to remove the light source and put a new light source in place.

In the boat drive and steer assembly as mentioned, in order to have complete anti-biofouling coverage of a surface of the propeller shaft casing, it is advantageous if the propeller shaft casing is designed so as to avoid a situation in which portions of the surface of the propeller shaft casing are in the shadow with respect to the rays of the anti-biofouling light from the light sources. In particular, it is possible to have a pointed appearance of a front end of the propeller shaft casing, which front end is known to be rounded in conventional situations. For the same reason of desiring to have complete anti-biofouling coverage, it is advantageous if at the position of transitions between the propeller shaft casing to a top portion of the fin, and also at the position of transitions between the propeller shaft casing to a housing part as present directly above the propeller shaft casing, smooth transition surfaces are provided, the transition surfaces being configured for allowing rays of anti-biofouling light emitted by the anti-biofouling system during operation of the at least one anti-biofouling light source thereof to skim along the surfaces.

Furthermore, the invention involves a new method of designing a device as mentioned, as the art does not teach adapting the configuration of the surfaces in such a way as to avoid as much as possible shadows with respect to the rays of anti-biofouling light from the at least one anti-biofouling light source of the anti-biofouling system, by means of which it is possible to have complete or near complete coverage of the surface to be subjected to an anti-biofouling action by the anti-biofouling system. In this respect, it is noted that the invention involves configuring surfaces in relation to emission characteristics of the at least one anti-biofouling light source of the anti-biofouling system, wherein it may particularly be so that the surfaces are oriented substantially parallel to and arranged alongside of a plane of rays of anti-biofouling light associated with operation of the at least one anti-biofouling light source. Such a design method may particularly be adapted to be used in respect of designing a device having both an anti-biofouling system and a plurality of functional elements, wherein the anti-biofouling system is provided with at least two anti-biofouling light sources for arrangement at different positions with respect to the plurality of functional elements, wherein surfaces of the functional elements, particularly surfaces which are to be subjected to an anti-biofouling action and which are blocked from directly facing at least one of the anti-biofouling light sources are provided with a planar appearance, and wherein a configuration of each one of those surfaces is determined in relation to emission characteristics of one of the anti-biofouling light sources, wherein particularly each one of those surfaces is oriented substantially parallel to and arranged alongside of a plane of rays of anti-biofouling light associated with operation of the at least one anti-biofouling light source.

The above-described and other aspects of the invention will be apparent from and elucidated with reference to the following detailed description of a number of embodiments of a device having surfaces to be subjected to an anti-biofouling action and an anti-biofouling system comprising at least one anti-biofouling light source for emitting rays of anti-biofouling light, in which device it is possible for the entire surface area thereof to be kept clean from biofouling when the anti-biofouling system is operated. The embodiments are just examples of numerous possible embodiments existing within the framework of the invention.

BRIEF DESCRIPTION OF THE DRAWINGS

The invention will now be explained in greater detail with reference to the figures, in which equal or similar parts are indicated by the same reference signs, and in which:

FIGS. 8 and 9 relate to a device according to a fourth practical embodiment of the invention, being a heat exchanger device and being equipped with an anti-biofouling system, wherein FIG. 8 diagrammatically shows a perspective view of two anti-biofouling light sources and a corrugated plate which are part of the device, and wherein FIG. 9 is based on FIG. 8 and shows a number of additional corrugated plates;

FIGS. 10 and 11 relate to a device according to a fifth practical embodiment of the invention, being a sterilizer box for a toothbrush and being equipped with an anti-biofouling system, wherein FIG. 10 diagrammatically shows a perspective top view of a basic part of an enclosure of the sterilizer box and an anti-biofouling light source as arranged inside the basic part, and wherein FIG. 11 illustrates a design of toothbrush supports as present inside the basic part.

The figures are of a diagrammatical nature only and are not necessarily drawn to scale.

DETAILED DESCRIPTION OF EMBODIMENTS

Figure 1:
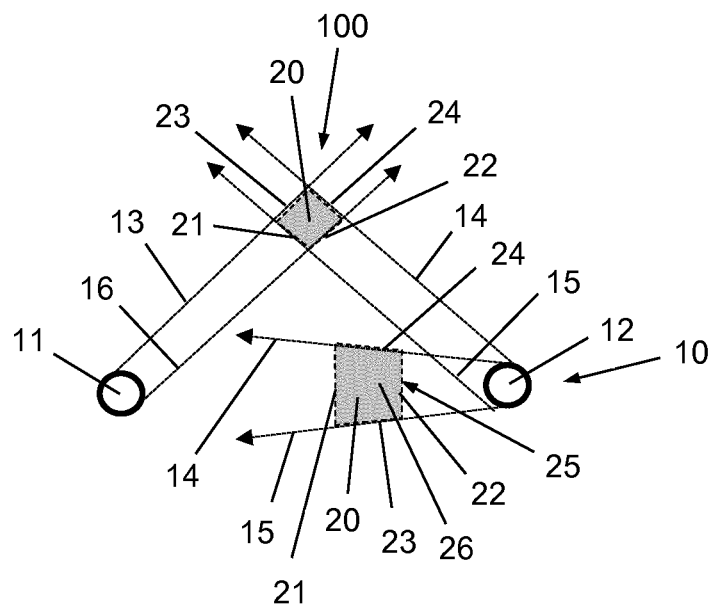
FIGS. 1 and 2 illustrate a basic principle of the invention, diagrammatically showing two anti-biofouling light sources for emitting anti-biofouling light and functional elements having surfaces to be subjected to an anti-biofouling action.
Figure 2:
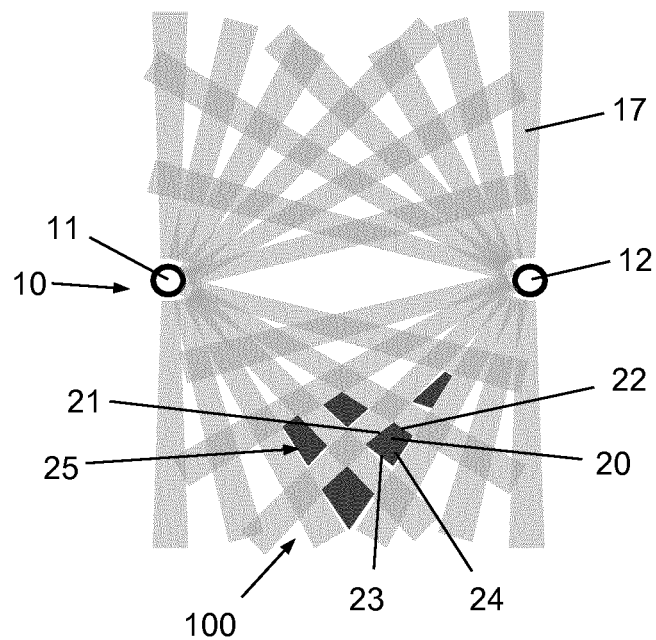

FIGS. 1 and 2 illustrate a basic principle of the invention, diagrammatically showing two anti-biofouling light sources 11, 12 for emitting anti-biofouling light and functional elements 20 having surfaces 21, 22, 23, 24 to be kept clean from biofouling. The anti-biofouling light sources 11, 12 and the functional elements 20 are part of a device 100, which, by way of example, is assumed to be a heat exchanger in the following, in which case the functional elements 20 can be assumed to be pipes for containing and transporting a fluid for exchanging heat with the pipes' surroundings. The collection of surfaces 21, 22, 23, 24 of all the pipes 20 make up a total surface area 25 of the heat exchanger 100, which total surface area 25 is to be kept clean from biofouling in order to preserve proper functioning of the heat exchanger 100. For the sake of completeness, it is noted that it follows from the foregoing that there does not need to be a (physical) connection between all of the surfaces 21, 22, 23, 24 making up the total surface area 25.

The anti-biofouling light sources 11, 12 are part of an anti-biofouling system 10 and are adapted to emit anti-biofouling light during operation. The anti-biofouling system 10 further comprises components such as means for controlling and driving the anti-biofouling light sources 11, 12, which components are not shown in any of the figures, as the invention does not particularly relate to those components. The anti-biofouling system 10 is suitable to be used for fulfilling the requirement of keeping the total surface area 25 of the heat exchanger 100 clean from biofouling, as mentioned in the foregoing. In a practical embodiment, the anti-biofouling light sources 11, 12 may be adapted to emit ultraviolet light during operation.

In the diagrammatic representation of FIG. 1, a sectional view is shown of the anti-biofouling light sources 11, 12 and two pipes 20. The anti-biofouling light sources 11, 12 may have an elongated shape, in which case the anti-biofouling light sources 11, 12 may be arranged so as to extend substantially parallel to the pipes 20. However, that does not alter the fact that the anti-biofouling light sources 11, 12 may have another appearance, such as an appearance in which the anti-biofouling light sources 11, 12 just have limited dimensions and are arranged at an appropriate level with respect to the pipes 20. In any case, the anti-biofouling light sources 11, 12 may be adapted to emit anti-biofouling light in all directions or in only a limited range, whatever is appropriate in a given situation. In general, the anti-biofouling system 10 may comprise at least one anti-biofouling light source 11, 12 of any suitable type, such as an ultraviolet lamp, possibly combined with one or more reflectors.

Each of the two pipes 20 as shown in FIG. 1 has four planar surfaces 21, 22, 23, 24 which are at the exterior of four flat side walls of the pipe 20 which are interconnected so as to surround an interior space 26 of the pipe 20, the cross-section of the pipe 20 having four corners. The pipe 20 as shown at the top of FIG. 1 has a more or less square cross-section, whereas the pipe 20 shown at the bottom of FIG. 1 has a trapezoidal cross-section. The reason for having pipes 20 of different shapes relates to configuration requirements of the invention as will now be explained.

The pipe 20 as shown at the top of FIG. 1, which will hereinafter be referred to as top pipe 20, has a first surface 21 which is in a position of directly facing the anti-biofouling light source 11 as depicted at the left side of FIG. 1, which will hereinafter be referred to as first anti-biofouling light source 11. Furthermore, the top pipe 20 has a second surface 22 which is in a position of directly facing the anti-biofouling light source 12 as depicted at the right side of FIG. 1, which will hereinafter be referred to as second anti-biofouling light source 12. The two remaining surfaces 23, 24 of the top pipe 20, i.e. a third surface 23 and a fourth surface 24 of the top pipe 20, are not in a position of directly facing an anti-biofouling light source 11, 12. Nevertheless, these surfaces 23, 24 are in a position of being subjected to an anti-biofouling action during operation of the anti-biofouling light sources 11, 12. The fact is that the third surface 23 is oriented substantially parallel to and arranged alongside of a plane 13 of rays of anti-biofouling light emitted by the first anti-biofouling light source 11 during operation, and that the fourth surface 24 is oriented substantially parallel to and arranged alongside of a plane 14 of rays of anti-biofouling light emitted by the second anti-biofouling light source 12 during operation. The planes 13, 14 of rays as mentioned are indicated by means of dashed arrows in FIG. 1. As a result of the specific configuration as explained in the foregoing, the third surface 23 and the fourth surface 24 of the top pipe 20 are subjected to an anti-biofouling treatment performed by rays of anti-biofouling light skimming along these surfaces 23, 24 during operation of the anti-biofouling light sources 11, 12. In that way, it is achieved that the surfaces 23, 24 can be kept free from biofouling even though they are not in a position of facing at least one of the anti-biofouling light sources 11, 12. The configuration of the top pipe 20 as shown is such that even if something would be in the way between the left anti-biofouling light source 11 and the first surface 21, the first surface 21 would still be subjected to an anti-biofouling action during operation of the anti-biofouling light sources 11, 12, as the first surface 21 is oriented substantially parallel to and arranged alongside of a plane 15 of rays of anti-biofouling light emitted by the second anti-biofouling light source 12 during operation. Similarly, even if something would be in the way between the second anti-biofouling light source 12 and the second surface 22, the second surface 22 would still be subjected to an anti-biofouling action during operation of the anti-biofouling light sources 11, 12, as the second surface 22 is oriented substantially parallel to and arranged alongside of a plane 16 of rays of anti-biofouling light emitted by the first anti-biofouling light source 11 during operation.

Like the top pipe 20, the pipe 20 shown at the bottom of FIG. 1, which will hereinafter be referred to as bottom pipe 20, comprises a first surface 21 facing the left anti-biofouling light source 11 and a second surface 22 facing the second anti-biofouling light source 12. However, as the bottom pipe 20 extends at a position which is between the anti-biofouling light sources 11, 12, the first surface 21 and the second surface 22 do not adjoin each other as is the case with the top pipe 20, but have an opposite positioning in the bottom pipe 20 instead. The two remaining surfaces 23, 24 are oriented substantially parallel to and arranged alongside of planes 14, 15 of rays of anti-biofouling light emitted by the second anti-biofouling light source 12 during operation. As an alternative, it is just as well possible for the two remaining surfaces 23, 24 to be oriented substantially parallel to and arranged alongside of planes 13, 16 of rays of anti-biofouling light emitted by the first anti-biofouling light source 11 during operation, as in such a case, a requirement of having such a configuration of the pipes 20 that none of the surfaces 21, 22, 23, 24 of the pipes 20 is in the shadow with respect to the rays of anti-biofouling light from the anti-biofouling light sources 11, 12 is also complied with. In the shown example, a surface 23, 24 of a pipe 20 which is not in a position of facing at least one anti-biofouling light source 11, 12 is still in a position of being subjected to an anti-biofouling action during operation of the anti-biofouling light sources 11, 12, namely an anti-biofouling action which involves rays of anti-biofouling light skimming along those surfaces 23, 24.

In the diagrammatic representation of FIG. 2, a sectional view is shown of the anti-biofouling light sources 11, 12 and five pipes 20 which may be assumed to be part of a larger collection of pipes 20 of which now only five are shown for the sake of clarity. FIG. 2 clearly illustrates the fact that each surface 21, 22, 23, 24 of each pipe 20 is oriented substantially parallel to and arranged alongside of a plane of rays of anti-biofouling light emitted by one of the anti-biofouling light sources 11, 12 during operation. In this way, it is achieved that the total surface area 25 of the heat exchanger 100 comprising the pipes 20 is subjected to an anti-biofouling action during operation of the anti-biofouling light sources 11, 12, as the anti-biofouling system 10 covers all of the surfaces 21, 22, 23, 24 of all of the pipes 20, wherein none of the surfaces 21, 22, 23, 24 is in the shadow with respect to the rays of anti-biofouling light from the anti-biofouling light sources 11, 12, regardless of whether a surface 21, 22, 23, 24 is part of a pipe 20 which is behind another pipe 20 as seen from one or both of the anti-biofouling light sources 11, 12, or not. For the sake of completeness, it is noted that in FIG. 2, bundles 17 of rays of anti-biofouling anti-biofouling light delimiting areas in which pipes 20 may be present are indicated as shaded thick lines. The five pipes 20 as shown are arranged between a number of those bundles 17, and are delimited by border planes of those bundles 17.

The invention is about realizing a device 100 having surfaces 21, 22, 23, 24 making up a total surface area 25 of the device 100 to be subjected to an anti-biofouling action and an anti-biofouling system 10 comprising at least one anti-biofouling light source 11, 12 for emitting rays of anti-biofouling light. In particular, the surfaces 21, 22, 23, 24 of the device 100 do not just have any shape, but are carefully configured so as to enable the total surface area 25 of the device 100, or at least a major portion of the total surface area 25, to be acted upon by the anti-biofouling system 10 during operation of the at least one anti-biofouling light source 11, 12 thereof. For example, the surfaces 21, 22, 23, 24 may have a planar appearance and may be oriented substantially parallel to and arranged alongside of a plane 13, 14, 15, 16 of rays of anti-biofouling light emitted by the anti-biofouling system 10 during operation of the at least one anti-biofouling light source 11, 12 thereof, as illustrated in FIGS. 1 and 2. In any case, according to the invention, the configuration of the surfaces 21, 22, 23, 24 is chosen such that none or only a minority of the surfaces is in the shadow with respect to the at rays of light from the least one anti-biofouling light source 11, 12, wherein it is possible to rely on the fact that having an arrangement of a surface 21, 22, 23, 24 in which rays of anti-biofouling light are allowed to skim along the surface 21, 22, 23, 24 is a feasible way of guaranteeing that the surface 21, 22, 23, 24 can be kept clean from biofouling.

FIGS. 3-9 relate to the application of the principle of the invention an actual heat exchanger device including an anti-biofouling system 10. In all of the figures, it can clearly be seen that a mutual arrangement of surfaces of elements of the heat exchanger device and anti-biofouling light sources 11, 12 of the anti-biofouling system 10 is chosen such that rays of anti-biofouling light emitted by the anti-biofouling light sources 11, 12 during operation are allowed to reach the surfaces by impacting on the surfaces at a certain angle and/or skimming along the surfaces, such that none of the surfaces is in the shadow with respect to the rays of anti-biofouling light from the anti-biofouling light sources 11, 12. In the examples shown in FIGS. 3-9, the elements of the heat exchanger device are mostly provided with planar surfaces which are at positions and orientations for being reached by skimming rays of the anti-biofouling light during operation of the anti-biofouling light sources 11, 12.

Figure 3:
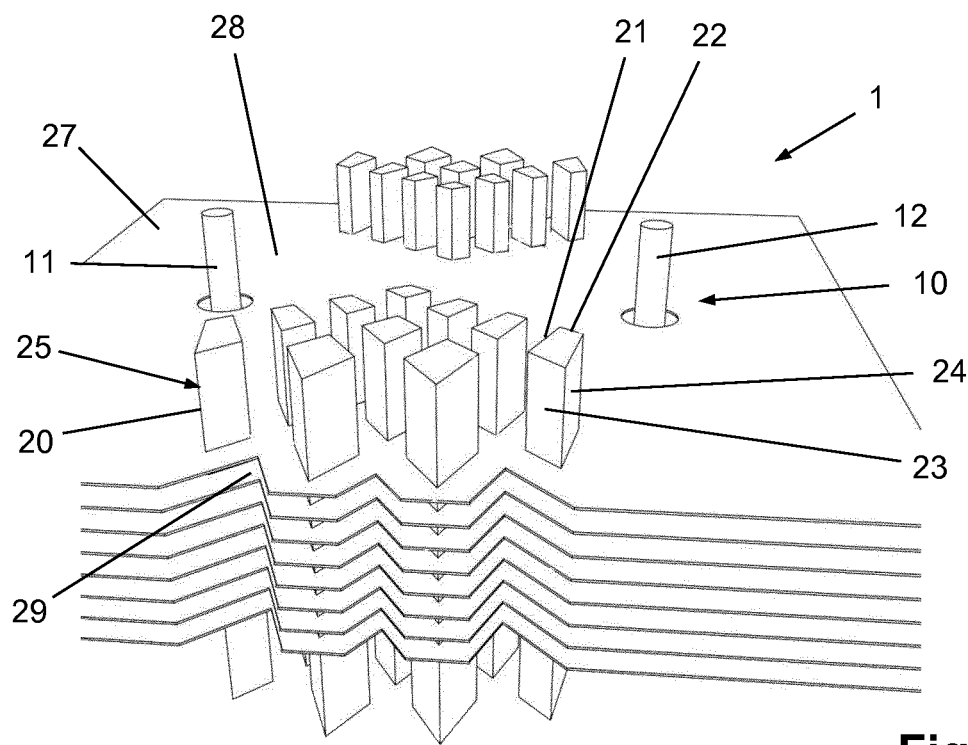
FIGS. 3 and 4 diagrammatically show a perspective view and a sectional view, respectively, of a device according to a first practical embodiment of the invention, being a heat exchanger device and being equipped with an anti-biofouling system.
Figure 4:
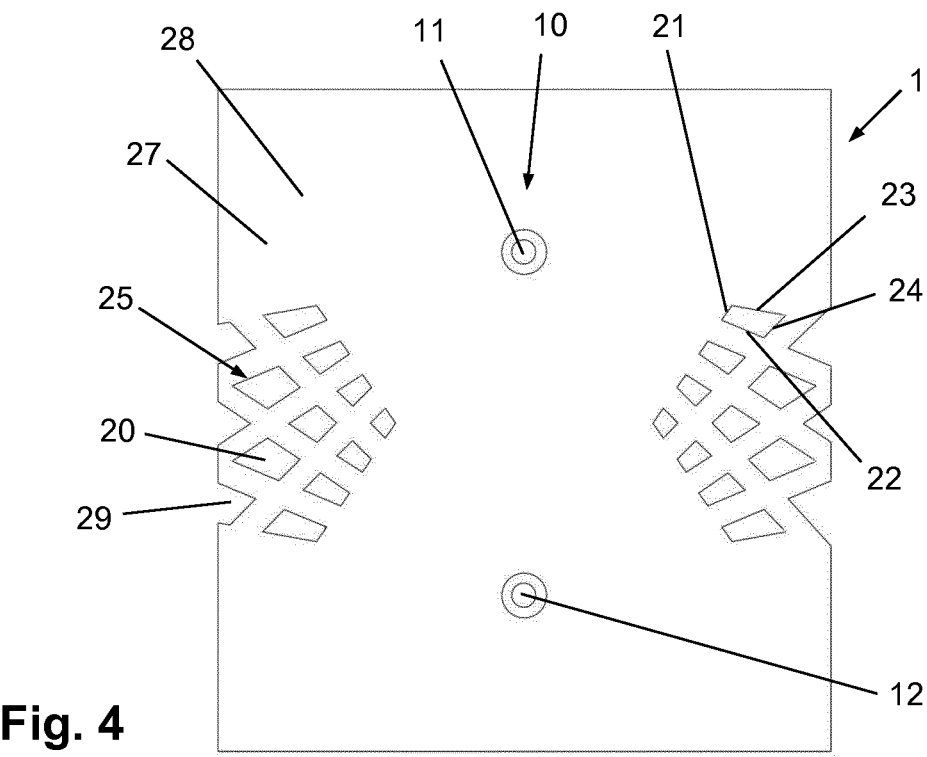

FIGS. 3 and 4 relate to a device 1 according to a first practical embodiment of the invention, being a heat exchanger device and being equipped with an anti-biofouling system 10. In this embodiment, the heat exchanger device 1 comprises a number of pipes 20 and a number of plates 27. The plates 27 have a planar appearance and arranged in a stack in which the plates 27 extend transversely to the pipes 20 at a regular mutual distance, i.e. at various levels with respect to the pipes 20 at a regular mutual distance. The pipes 20 serve for containing and transporting a fluid for exchanging heat with a fluid surrounding the pipes 20 and the plates 27, the plates 27 being in contact with the pipes 20 and having a function in enlarging the heat exchanger area. Advantageously, both the pipes 20 and the plates 27 are made of a material having excellent thermal conductivity. The anti-biofouling system 10 comprises two elongated anti-biofouling light sources 11, 12 extending substantially parallel to each other and to the pipes 20. The anti-biofouling light sources 11, 12 are arranged at a distance with respect to each other, and the pipes 20 are arranged in two groups arranged at a distance at either side of an imaginary plane including longitudinal axes of both anti-biofouling light sources 11, 12.

It can be seen in FIGS. 3 and 4 that surfaces 21, 22, 23, 24 of the pipes 20 are configured so as to be oriented substantially parallel to and arranged alongside of planes of rays of anti-biofouling light emitted by the anti-biofouling light sources 11, 12 during operation. For the sake of completeness, it is noted that this implies that the surfaces 21, 22, 23, 24 of the pipes 20 are configured so as to be oriented substantially parallel to and arranged alongside of imaginary planes extending from the anti-biofouling light sources 11, 12 and being oriented in both a longitudinal direction and a radial direction with respect to the anti-biofouling light sources 11, 12. In this configuration, the cross-section of each of the pipes 20 has a polygonal shape, particularly a trapezoidal shape. This is significantly different from known heat exchanger devices having pipes 20, in which the pipes 20 normally have a round periphery. The configuration of the pipes 20 as arranged in the groups is such that all of the surfaces 21, 22, 23, 24 of each of the pipes 20 is covered by the anti-biofouling system 10, wherein none of those surfaces 21, 22, 23, 24 is in the shadow with respect to the rays of anti-biofouling light from the anti-biofouling light sources 11, 12, due to the application of the configuration principle as explained, which will hereinafter be referred to as the skimming principle. Assuming that the plates 27 extend substantially perpendicular to the anti-biofouling light sources 11, 12 and the pipes 20, the plates 27 are not in a position of throwing shadows on any of the surfaces 21, 22, 23, 24 of any of the pipes 20 either, while it is ensured in this way that the entire surface 28 of each of the plates 27 is irradiated with rays of anti-biofouling light during operation of the anti-biofouling light sources 11, 12, both rays impacting on the plates 27 at an angle and rays skimming along the plates 27. A notable feature of the configuration of the plates 27 resides in the fact that areas of the plates 27 which are positioned behind the groups of pipes 20 as seen from the anti-biofouling light sources 11, 12 and which are not covered by a bundle of rays of anti-biofouling light passing between the pipes 20 during operation of the anti-biofouling light sources 11, 12 are removed, which results in edges of the plates 27 being provided with notches 29, so that it is ensured that not any spot of the heat exchanger device 1 is in the shadow with respect to the anti-biofouling light sources 11, 12, which has as an advantageous consequence that the total surface area 21, 22, 23, 24, 28 of the heat exchanger device 1 can be kept free from biofouling, without a need to apply more than just two anti-biofouling light sources 11, 12.

Figure 5:
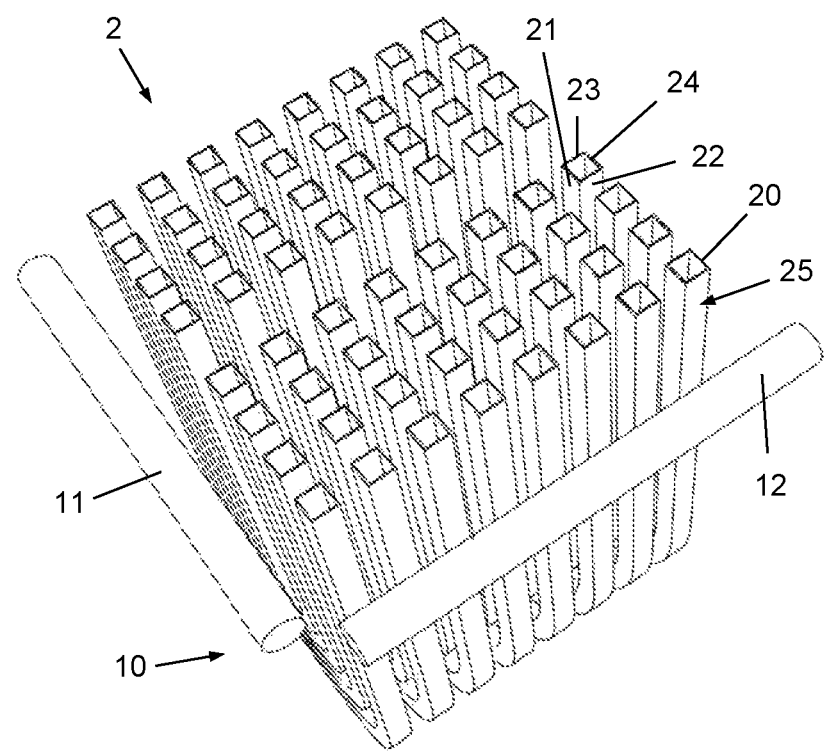
FIG. 5 diagrammatically shows a perspective top view of a plurality of U shaped pipes and elongated anti-biofouling light sources for emitting anti-biofouling light, which are part of a device according to a second practical embodiment of the invention, being a heat exchanger device and being equipped with an anti-biofouling system.

FIG. 5 relates to a device 2 according to a second practical embodiment of the invention, being a heat exchanger device and being equipped with an anti-biofouling system 10. In this embodiment, the heat exchanger device 2 is a box cooler, comprising bundles of U shaped pipes 20 as shown in FIG. 5. Furthermore, in this embodiment, only two anti-biofouling light sources 11, 12 are applied for keeping all of the surfaces 21, 22, 23, 24 of straight portions of all of the pipes 20 free from biofouling. For the sake of completeness, it is noted that possible further anti-biofouling light sources, which may be applied for keeping all of the surfaces 21, 22, 23, 24 of curved portions of all the pipes 20 free from biofouling, are not shown in FIG. 5, and that the following description is particularly applicable to the part of the heat exchanger device 2 where the straight portions of the pipes 20 are located. On the other hand, an alternative embodiment of a box cooler is feasible within the framework of the invention, in which the part of the box cooler where originally the curved portions of the pipes 20 are present is redesigned. For example, it is possible to apply a common box for all the straight portions of the pipes 20 to extend to, which box may be delimited by planar surfaces only.

The anti-biofouling light sources 11, 12 have an elongated shape and are arranged so as to extend alongside the bundles of U shaped pipes 20, at a level of the straight portions of the pipes 20, wherein the anti-biofouling light sources 11, 12 are both substantially perpendicular to each other and perpendicular to the straight portions of the pipes 20, like the x, y and z axis of a coordinate system. The pipes 20 have a square cross-section, and the straight portions of the pipes 20 extend in straight rows in a regular pattern, as clearly shown in FIG. 5, so that it is achieved that all of the surfaces 21, 22, 23, 24 of all of the straight portions of the pipes 20 are at a position for allowing rays of anti-biofouling light emitted by the anti-biofouling light sources 11, 12 during operation to skim along the surfaces 21, 22, 23, 24 as mentioned. The configuration of the straight portions of the pipes 20 according to the skimming principle is the basis of guaranteeing complete coverage of the total surface area 25 of the heat exchanger device 2 by the anti-biofouling system 10 at the level of the straight portions of the pipes 20. Furthermore, rays impacting on the surfaces 21, 22, 23, 24 of the straight portions of the pipes 20 at an angle have an anti-biofouling effect on the total surface area 25 as well, but as a general rule, the more a straight portion of a pipe 20 is remote from the anti-biofouling light sources 11, 12, the more the anti-biofouling action is realized by rays skimming along the surfaces 21, 22, 23, 24 of the straight portion of the pipe 20 during operation of the anti-biofouling light sources 11, 12.

When a comparison between the device 1 according to the first practical embodiment of the invention and the device 2 according to the second practical embodiment of the invention is made, it is found that an advantage of the first embodiment over the second embodiment is found in the fact that the anti-biofouling light sources 11, 12 may be easily replaced by moving them in the longitudinal direction to one side of the heat exchanger device 1, and that an advantage of the second embodiment over the first embodiment is found in the fact all of the pipes 20 have the same cross-section, which facilitates the manufacturing process of the heat exchanger device 2.

Figure 6:
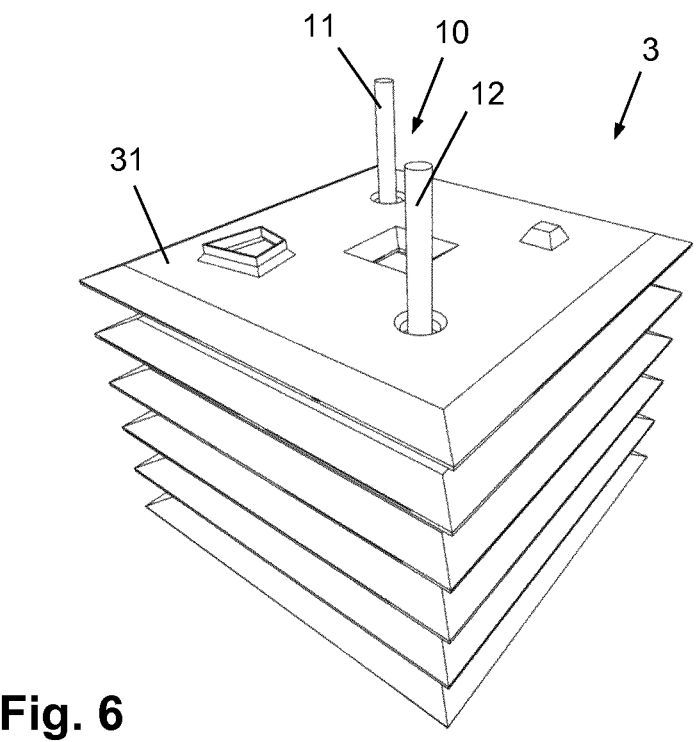
FIGS. 6 and 7 relate to a device according to a third practical embodiment of the invention, being a heat exchanger device and being equipped with an anti-biofouling system, wherein FIG. 6 diagrammatically shows a perspective view of the device, and wherein FIG. 7 diagrammatically shows an exploded view of two heat exchanger units which are part of the device.
Figure 7:
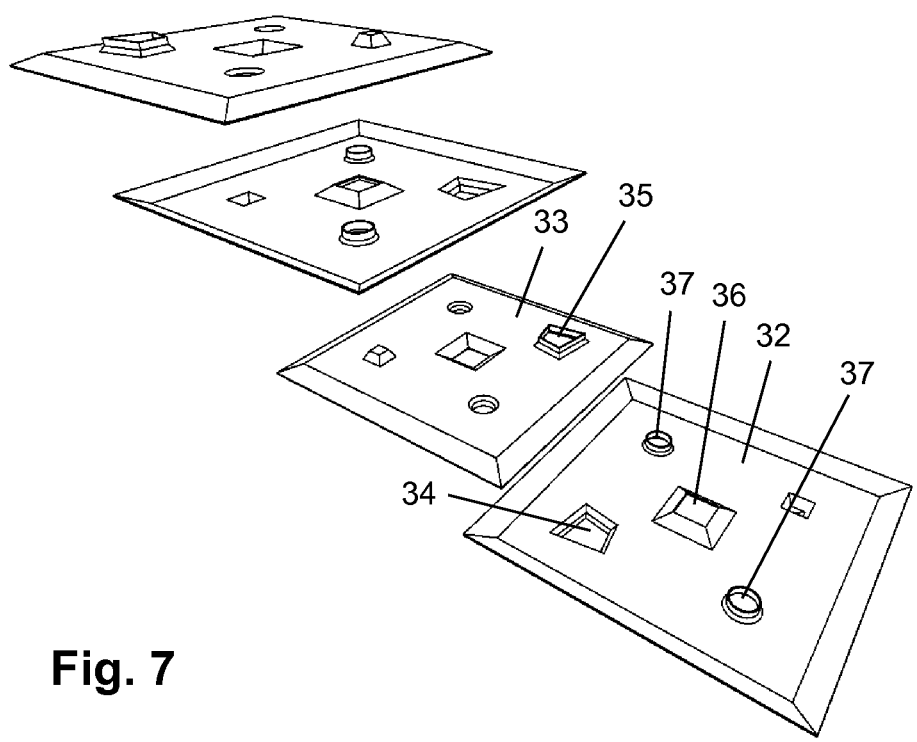

FIGS. 6 and 7 relate to a device 3 according to a third practical embodiment of the invention, being a heat exchanger device and being equipped with an anti-biofouling system 10. In this embodiment, the heat exchanger device 3 is a plate cooler, comprising a number of interconnected units 31 in successive arrangement, the units 31 having a plate-like appearance. In the shown example, the units 31 are stacked at a regular mutual distance, and are adapted to contain and transport fluid for exchanging heat with fluid surrounding the units 31. On the basis of this set-up, the heat exchanger device 3 is suitable to be used in a marine environment, for example, wherein the device 3 may be arranged inside a sea chest of a vessel, in which case the fluid surrounding the units 31 during operation is seawater. Each of the units 31 is composed of two shallow tray-like halves 32, 33 which are sealingly connected to each other along their periphery, as is apparent from the exploded view of two units 31 as diagrammatically shown in FIG. 7. In the assembled condition, each unit 31 has an interior space, an inlet 34 for supplying fluid to the interior space, and an outlet 35 for discharging fluid from the interior space, wherein the outlet 35 is offset from the inlet 34 for the purpose of avoiding a situation in which fluid entering the unit 31 immediately exits the unit 31, in which situation the unit 31 would not be effective in allowing for exchange of heat. Thus, in the stack of units 31, the fluid flowing through the units 31 is forced to follow a staggered route, which is beneficial to the heat exchanging process. The heat exchanger device 3 may be equipped with a pump (not shown) or the like for realizing the necessary flow of fluid from one unit 31 to another, all the way down the entire device 3. Besides holes of the inlet 34 and the outlet 35, each unit 31 comprises a central hole 36 for allowing fluid from the surroundings to pass through, and two holes 37 for allowing elongated anti-biofouling light sources 11, 12 of the anti-biofouling system 10 to pass through. In the shown example, only two elongated anti-biofouling light sources 11, 12 are used with the heat exchanger device 3, both anti-biofouling light sources 11, 12 extending through all of the units 31, in a direction which is substantially perpendicular to the plane shape of the units 31.

In FIGS. 6 and 7, it can be seen that various surfaces of the units 31 are configured according to the skimming principle. For example, standing surfaces which are present at the inlet 34 and the outlet 35, respectively, are planar and are oriented substantially parallel to and arranged alongside a plane of rays of anti-biofouling light emitted by the anti-biofouling light sources 11, 12 during operation. As a consequence, the holes of the inlet 34 and the outlet 35 are not simply round or rectangular, but have a trapezoidal shape. Also, the halves 32, 33 making up the units 31 have beveled side edges for the reason of avoiding a situation of having transverse side edges which would be in the shadow with respect to the rays of anti-biofouling light from the anti-biofouling light sources 11, 12.

Figure 8:
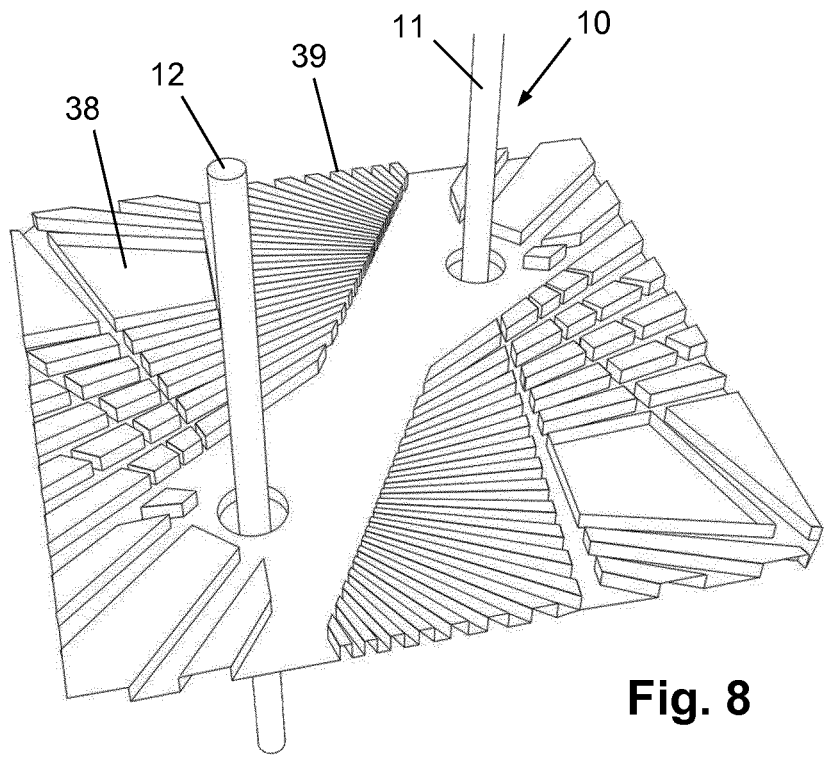
Figure 9:
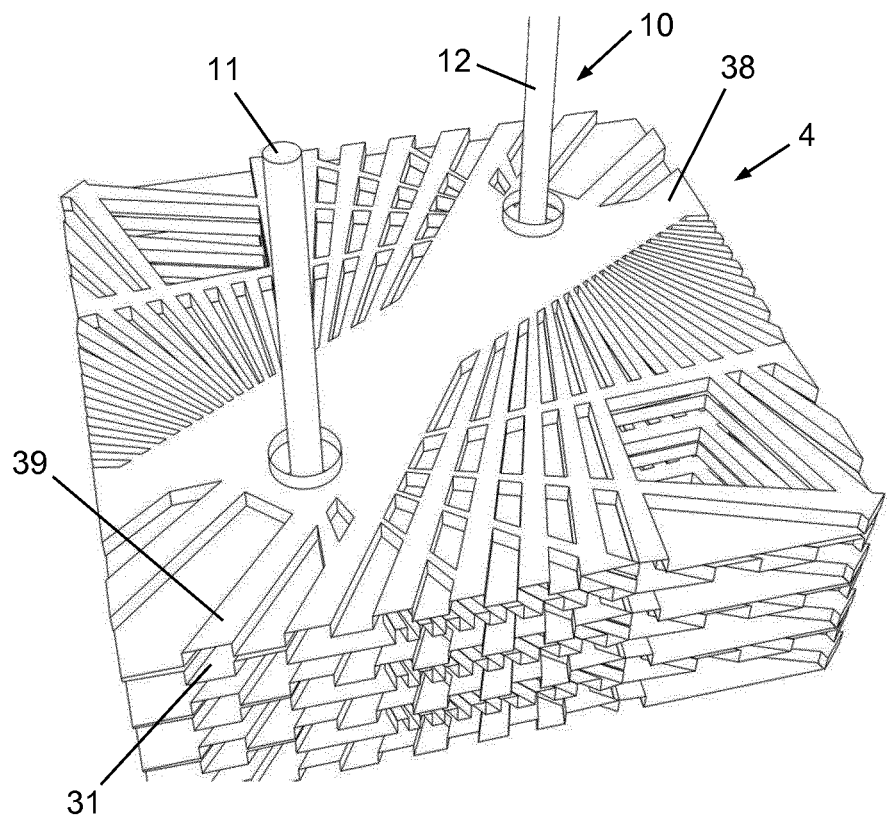

FIGS. 8 and 9 relate to a device 4 according to a fourth practical embodiment of the invention, being a heat exchanger device and being equipped with an anti-biofouling system 10. The heat exchanger device 4 of this embodiment is a plate cooler, which is of another type than the plate cooler illustrated by means of FIGS. 6 and 7. In particular, in this case, the plate cooler 4 comprises a stack of corrugated sheets 38 for delimiting the units 31 of the plate cooler 4, wherein a configuration is realized in which units 31 of a first group of units 31 for containing and transporting a first fluid alternate with units 31 of a second group of units 31 for containing and transporting a second fluid, so that heat exchange between the first fluid and the second fluid can take place in an optimal manner. Also in this device 4 according to the invention, only two anti-biofouling light sources 11, 12 are used for realizing anti-biofouling of the entirety of the plate cooler 4, the anti-biofouling light sources 11, 12 extending through the entire stack of corrugated sheets 38, in a direction which is substantially perpendicular to the plane shape of the corrugated sheets 38.

Corrugations 39 which are part of the corrugated sheets 38 have a primary function of defining channels on the corrugated sheets, thereby enlarging the heat exchanger area of the plate cooler 4, and may also serve for determining a mutual distance between the sheets 38 in the stack. In order to avoid any shadowing action of the corrugations 39 on any spot or area of the corrugated sheets 38, the corrugations 39 are configured according to the skimming principle. Hence, the corrugations 39 extend in a straight direction along an imaginary plane extending from one of the anti-biofouling light sources 11, 12 and being oriented in both a longitudinal direction and a radial direction with respect to the anti-biofouling light sources 11, 12. FIGS. 8 and 9 clearly illustrate the fact that the way in which groups of corrugations 39 are arranged with respect to the respective anti-biofouling light sources 11, 12 resembles a configuration of rays shining from a light source. It is a notable achievement of the invention that even a relatively complex device such as a plate cooler 3, 4 comprising a stack of corrugated sheets 38 can be kept clean from biofouling by using no more than two elongated anti-biofouling light sources 11, 12, as long as the configuration of all surfaces of the plate cooler 3, 4 is adjusted in a way which is appropriate for realizing total or near-total coverage of the surfaces by the anti-biofouling system 10. In principle, according to the invention, depending on the desired configuration of functional elements 20, 27, 31, 38 of a device, it may even be sufficient to apply only one anti-biofouling light source 11, 12 in certain cases.

It will be clear to a person skilled in the art that the scope of the invention is not limited to the examples discussed in the foregoing, but that several amendments and modifications thereof are possible without deviating from the scope of the invention as defined in the attached claims. It is intended that the invention be construed as including all such amendments and modifications insofar they come within the scope of the claims or the equivalents thereof. While the invention has been illustrated and described in detail in the figures and the description, such illustration and description are to be considered illustrative or exemplary only, and not restrictive. The invention is not limited to the disclosed embodiments. The drawings are schematic, wherein details that are not required for understanding the invention may have been omitted, and not necessarily to scale.

Variations to the disclosed embodiments can be understood and effected by a person skilled in the art in practicing the claimed invention, from a study of the figures, the description and the attached claims. In the claims, the word "comprising" does not exclude other steps or elements, and the indefinite article "a" or "an" does not exclude a plurality. Any reference signs in the claims should not be construed as limiting the scope of the invention. The phrase "a plurality of" as used in this text should be understood such as to mean "at least two".

Elements and aspects discussed for or in relation with a particular embodiment may be suitably combined with elements and aspects of other embodiments, unless explicitly stated otherwise. Thus, the mere fact that certain measures are recited in mutually different dependent claims does not indicate that a combination of these measures cannot be used to advantage.

The term "substantially" as used in this text will be understood by a person skilled in the art as being applicable to situations in which a certain effect is intended which can be fully realized in theory but which involves practical margins for its factual implementation. Examples of such an effect include a parallel arrangement of objects and a perpendicular arrangement of objects. Where applicable, the term "substantially" may be understood such as to be an adjective which is indicative of a percentage of 90% or higher, such as 95% or higher, especially 99% or higher, even more especially 99.5% or higher, including 100%.

The term "comprise" as used in this text will be understood by a person skilled in the art as covering the term "consist of". Hence, the term "comprise" may in respect of an embodiment mean "consist of", but may in another embodiment mean "contain/include at least the defined species and optionally one or more other species".

The invention is relevant in every situation in which surfaces making up a total surface area of a device are exposed, during at least a part of their lifetime, to a fluid that is apt to cause biofouling of the surfaces. As can be derived from the disclosed embodiments, a practical application of the invention is an application in the field of appliances for use in an industrial environment, which may be a marine environment. Another practical application of the invention is an application in the field of domestic appliances. For example, the invention may be put to practice in reservoirs of coffee makers, in casings of kitchen appliances, in boxes for sterilizing personal care appliances such as toothbrushes, in cleaning accessories of shavers or other hair removal devices, etc. In this respect, one feasible example is illustrated by means of FIGS. 10 and 11, which relate to a device 5 according to a fifth practical embodiment of the invention, being a sterilizer box for accommodating and sterilizing a toothbrush (not shown) and being equipped with an anti-biofouling system 10, wherein the anti-biofouling system 10 comprises a single tubular ultraviolet lamp 11. In the shown example, the sterilizer box 5 comprises an enclosure 51 having an interior surface 52, which enclosure 51 is shaped like a box, and which enclosure 51 consists of a basic part 53 and a cover part (not shown), wherein the basic part 53 is designed for actually receiving a toothbrush, being equipped with toothbrush supports 54, 55 which are functional elements of the sterilizer box 5 having a function in supporting a toothbrush in an appropriate positioning inside the sterilizer box 5, and wherein the tubular ultraviolet lamp 11 is arranged inside the basic part 53. The cover part has any suitable movable arrangement with respect to the basic part 53, for allowing an opened state of the basic part 53 and a closed state of the basic part 53, as necessary for allowing insertion and removal of a toothbrush, and for shielding the environment of the sterilizer box 5 from ultraviolet light during operation of the sterilizer box 5, respectively. For example, the cover part may be hingably attached to the basic part 53, may be slidable with respect to the basic part 53, or may be removable from the basic part 53. For the sake of completeness, it is noted that in FIG. 11, the tubular ultraviolet lamp 11 and the toothbrush supports 54, 55, being interior elements of the sterilizer box 5, are indicated by means of dashed lines.

According to the invention, measures are taken in order to avoid a situation in which one or more areas of the interior surface 52 of the enclosure 51 of the sterilizer box 5 are in the shadow with respect to the rays of ultraviolet light from the tubular ultraviolet lamp 11. Also, measures are taken in order to avoid a situation in which one or more surfaces or areas of surfaces of the toothbrush supports 54, 55 are in the shadow with respect to the rays of ultraviolet light from the tubular ultraviolet lamp 11. In fact, if the toothbrush supports 54, 55 would not be present inside the enclosure 51 of the sterilizer box 5, practically the entire interior surface 52 of the enclosure 51 could easily be irradiated with rays of ultraviolet light from the one tubular ultraviolet lamp 11. However, with the toothbrush supports 54, 55 being present inside the enclosure 51, it would be so that areas of the interior surface 52 of the enclosure would be in the shadow with respect to the rays of ultraviolet light from the tubular ultraviolet lamp 11, and the same would be the case with areas of the surfaces of the toothbrush supports 54, 55, if it was not for the measures according to the invention being applied.

Figure 10:
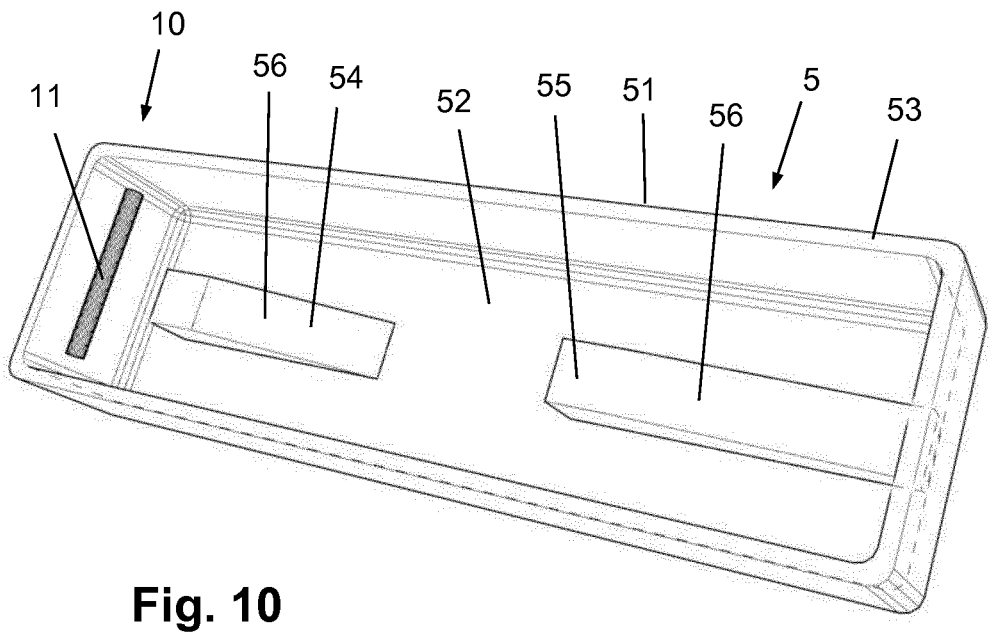
Figure 11:
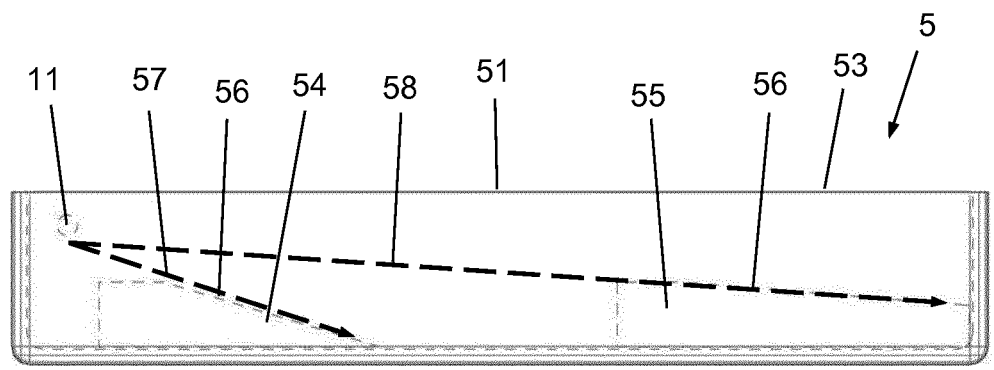

In FIG. 10, it can be seen that a number of surfaces of the toothbrush supports 54, 55 are designed so as to extend in a direction which is perpendicular to a longitudinal direction in which the tubular ultraviolet lamp 11 extends. As can be seen in both FIGS. 10 and 11, a top surface 56 of the toothbrush support 54 which is located closest to the tubular ultraviolet lamp 11 has a slanting design in the direction away from the tubular ultraviolet lamp 11, all the way down to the interior surface 52 of the enclosure 51, so that there is no back side of the toothbrush support 54 which would otherwise be in the shadow with respect to the rays of ultraviolet light from the tubular ultraviolet lamp 11, which is located at a relatively high level in the basic part 53. The slanting portion of the surface 56 as mentioned is made so as to extend alongside a plane 57 of ultraviolet rays from the tubular ultraviolet lamp 11, as diagrammatically indicated in FIG. 11 by means of a first dashed arrow. Similarly, a top surface 56 of the other toothbrush support 55 has a slanting design in the direction away from the tubular lamp 11, and extends alongside a plane 58 of ultraviolet rays from the tubular ultraviolet lamp 11, as diagrammatically indicated in FIG. 11 by means of a second dashed arrow. At a back side thereof, the other toothbrush support 55 is connected to the enclosure 51, as a result of which the toothbrush support 55 is free from any area which would otherwise be in the shadow with respect to the rays of ultraviolet light from the tubular ultraviolet lamp 11. Thus, both the design of the enclosure 51, involving a box shape of the enclosure 51 with an interior surface 52 having only planar areas, and the design of the toothbrush supports 54, 55 as explained in the foregoing, with only planar surfaces extending so that all of the surfaces can be reached by rays of ultraviolet light from the tubular ultraviolet lamp 11, wherein the rays are allowed to impact on the surfaces at an angle and/or to act on the surfaces in a skimming fashion, it is achieved that the sterilizer box 5 does not have any area which is not subjected to an anti-biofouling action by means of the ultraviolet light, so that the sterilizer box 5 is most hygienic, being free from potential hotbeds of microorganisms.

Within the framework of the invention, many features of the sterilizer box 5 can be varied, including the number of ultraviolet light sources 11, 12 and/or the number of toothbrush supports 54, 55, the type of the ultraviolet light source(s) 11, 12, and the shape of the toothbrush support(s) 54, 55, wherein the sterilizer box 5 can be designed so as to be suitable for sterilizing one toothbrush at a time or for sterilizing more than one toothbrush at a time, whatever is desired in a certain situation, as long as it is ensured that the configuration of surfaces 52, 56 as present inside the sterilizer box 5 and the at least one ultraviolet light source 11, 12 allows for realizing an anti-biofouling action on at least a majority of those surfaces 52, 56. This is done by carefully checking during the designing process whether all areas of all surfaces 52, 56 can be reached by the ultraviolet light from the at least one ultraviolet light source 11, 12, wherein the skimming principle is applied to one or more areas of the surfaces 52, 56 when it appears to be practical to do so.

Figure 12:
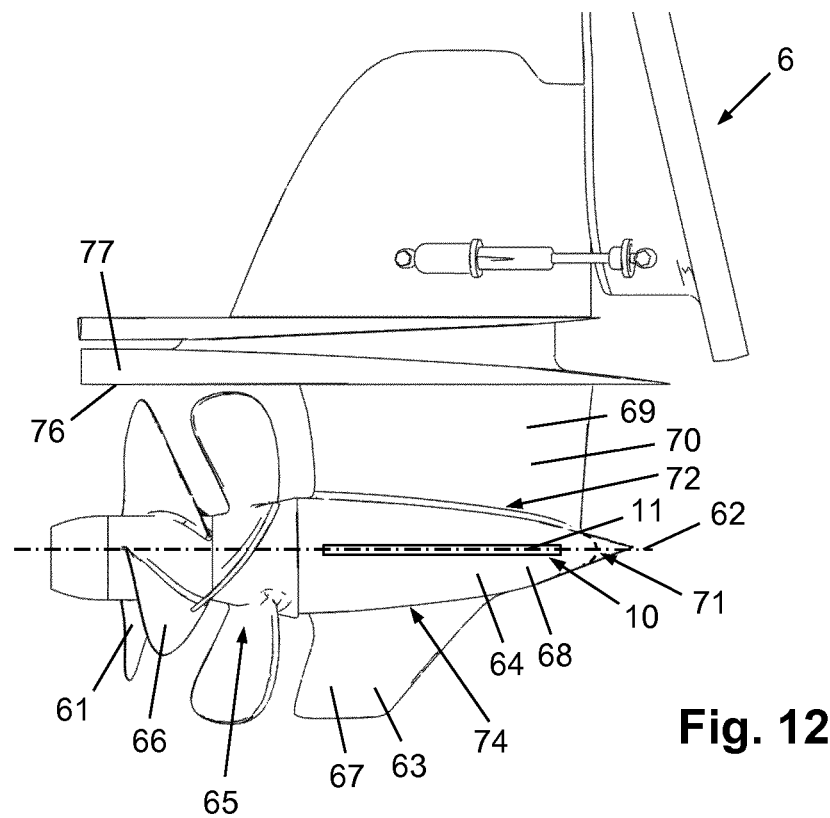
FIGS. 12-14 relate to a device according to a sixth practical embodiment of the invention, being a boat drive and steer assembly including a propeller and a fin, and being equipped with an anti-biofouling system, wherein FIG. 12 diagrammatically shows a side view of the assembly, wherein FIG. 13 diagrammatically shows a back view of the assembly, and wherein FIG. 14 diagrammatically shows a perspective view of the assembly, with a different positioning of light sources of the anti-biofouling system than shown in FIGS. 12 and 13.
Figure 13:
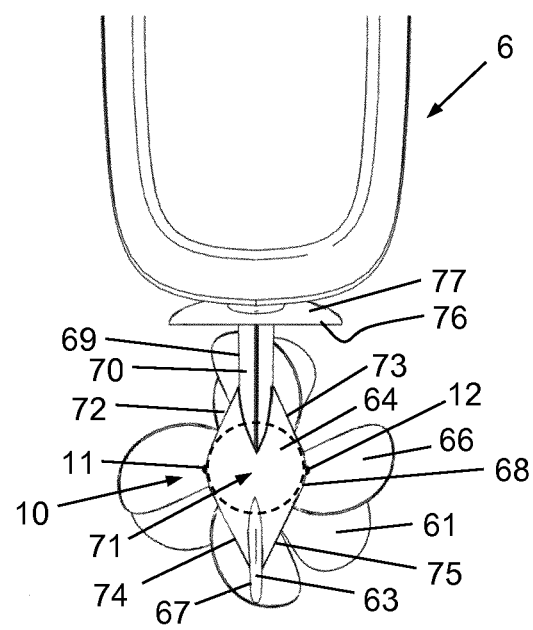
Figure 14:
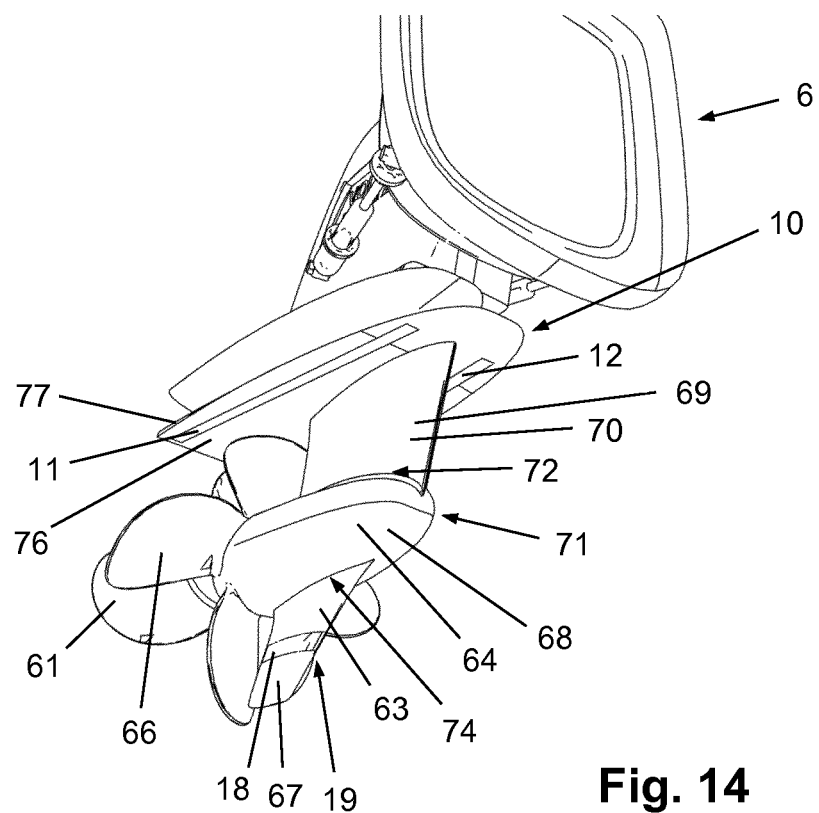

Yet another practical application of the invention is an application in the field of boat drive and steer assemblies. FIGS. 12-14 relate to one feasible example of a boat drive and steer assembly 6, which is also known as stern drive, and which is intended for arrangement at the back of a boat. A main component of the assembly 6 is a rotatable propeller 61 which is configured to realize propulsion of a boat when the assembly 6 is properly fixed to the boat and the boat is in the water. A rotation axis of the propeller 61 is diagrammatically depicted in FIG. 12 by means of a dash-and-dot line and indicated by means of reference numeral 62. Another main component of the assembly 6 is a fin 63 which is arranged at a position in front of the propeller 61. The fin 63 extends downwardly from a propeller shaft casing 64 which serves for accommodating a shaft 65 of the propeller 61 and associated gearing. Boat drive and steer assemblies such as stern drives are well known, and therefore, only the details of the assembly 6 shown in FIGS. 12-14 which are relevant in the context of the invention will be explained.

FIGS. 12 and 13 illustrate a first practical way in which the invention may be applied for the purpose of realizing anti-biofouling of portions of the boat drive and steer assembly 6, including surfaces 66, 67, 68 of the propeller 61, the fin 63 and the propeller shaft casing 64, respectively. In the shown example, an anti-biofouling system 10 comprising two elongated light sources 11, 12 which are arranged at opposite sides of the propeller shaft casing 64, and which extend in the direction of the rotation axis 62 of the propeller 61, is provided. The light sources 11, 12 may be provided in the form of an array of lamps such as LEDs, for example. During operation, the anti-biofouling light emitted by the light sources 11, 12 is used for keeping the surfaces 66, 67, 68 of the propeller 61, the fin 63 and the propeller shaft casing 64, respectively, and also other surfaces of the assembly 6, particularly surfaces which are present above the propeller shaft casing 64, such as a surface 69 of a housing part 70 to which the propeller shaft casing 64 is connected, clean from biofouling. The anti-biofouling effect on the surface 66 of the propeller 61 is optimal when the propeller 61 is rotated, as in that case, all portions of the propeller 61 are placed under the influence of the anti-biofouling system 10 in a continually alternating manner and are thereby treated in a more or less equal manner.

According to the invention, in order to allow the anti-biofouling light to cover the various surfaces 66, 67, 68, 69 of the boat drive and steer assembly 6 to an improved extent, the design of those surfaces 66, 67, 68, 69 is adapted with respect to a conventional design, i.e. a design which is commonly applied hitherto. For example, FIG. 12 illustrates the fact that a front end 71 of the propeller shaft casing 64 normally has a rounded appearance, as a result of which the surface 68 of the propeller shaft casing 64 would not be covered by the anti-biofouling light at the position of the front end 71. In order to have complete coverage of the surface 68 of the propeller shaft casing 64, it is advantageous to have a pointed appearance of the front end 71 as shown in FIG. 12, so that a situation in which portions of the surface 68 of the propeller shaft casing 64 are in the shadow with respect to the rays of the anti-biofouling light from the light sources 11, 12 is avoided. Furthermore, it is advantageous to have an adapted design at the position of transitions between the propeller shaft casing 64 to a top portion of the fin 63, and also at the position of transitions between the propeller shaft casing 64 to the housing part 70 as present directly above the propeller shaft casing 64. In the conventional design, the transitions have a generally concave appearance at a position with respect to the light sources 11, 12 in which it is not possible for the rays of the anti-biofouling light to reach the transitions, being blocked from doing so by convexly curved portions of the propeller shaft casing 64, as a result of which a situation is obtained in which shadow pits are present at the position of the transitions. Needless to say that those shadow pits are susceptible to biofouling to a very high extent, and that as the biofouling gets more and more, the drag of the assembly 6 is substantially increased. In order to avoid such a situation, it is proposed to have smooth transition surfaces 72, 73, 74, 75 at the various transitions, having such an orientation that rays of the anti-biofouling light are allowed to skim along the surfaces 72, 73, 74, 75. It is recognized that the presence of such surfaces 72, 73, 74, 75 may involve an increase of drag with respect to the conventional design, but as that increase can be expected to be significantly lower than an increase associated with biofouling in the conventional situation, it is still advantageous to have such surfaces 72, 73, 74, 75.

It is furthermore possible to have an adjustment of the design of the propeller 61 in order to realize that improved anti-biofouling coverage of the surface 66 of the propeller 61 is obtained. In the process, it is advantageous to find an optimum between design requirements relating to the driving function of the propeller 61 and design requirements relating to the anti-biofouling coverage of the surface 66 of the propeller 61, taking into account the fact that biofouling of the propeller 61 results in deterioration of the driving function. In order to enhance the anti-biofouling effects, it is a practical option to apply material that is highly reflective to the anti-biofouling light at the surface 66 of the propeller 61 and/or at one or more other appropriate surfaces 67, 68, 69, of the boat drive and steer assembly 6.

In the boat drive and steer assembly 6, the anti-biofouling system 10 may comprise any suitable number of light sources 11, 12, and various possibilities are available when it comes to positioning the at least one light source 11, 12 of the system 10 in the assembly 6. For example, one or more light sources 11, 12 may be positioned on the fin 63 and/or the housing part 70 as present directly above the propeller shaft casing 64 and/or one or more other parts of the assembly 6, such as a bottom surface 76 of a plate-like element 77 to which the housing part 70 is connected at a top side thereof. In this respect, it is noted that FIG. 14 illustrates a second practical way in which the invention may be applied for the purpose of realizing anti-biofouling of portions of the assembly 6. In the configuration shown in FIG. 14, two elongated light sources 11, 12 are arranged on the bottom surface 76 of the plate-like element 77 mentioned earlier, extending along a substantial part of the length thereof, at a port position and a starboard position in the assembly 6, respectively, and two elongated light sources 18, 19 are arranged on the fin 63, at opposite sides thereof. Furthermore, it is noted that it is also possible to provide a hollow propeller shaft 65, to apply material that is transparent to the anti-biofouling light in the propeller shaft 65, to use an elongated light source, and to arrange such light source so as to extend through the hollow propeller shaft 65, for the purpose of keeping the surface 66 of the propeller 61 clean from biofouling. On the other hand, it is a possibility to add elements to the design of the assembly 6 for the purpose of holding one or more light sources 11, 12, 18, 19 at positions which are advantageous as far as improving anti-biofouling coverage of one or more surfaces 66, 67, 68, 69, 72, 73, 74, 75, 76 of the assembly 6 is concerned. In any case, it is desirable to have a design which involves only a minimum number of light sources 11, 12, 18, 19 wherein the shape of the various surfaces 66, 67, 68, 69, 72, 73, 74, 75, 76 to be kept clean from biofouling is adapted to the requirement to avoid shadows as much as possible, wherein surfaces may be configured so as to allow rays of the anti-biofouling light to skim along those surfaces.

The light sources 11, 12, 18, 19 of the anti-biofouling system 10 used with the boat drive and steer assembly 6 may be controlled in any suitable manner. For example, it is possible to realize a relation between the intensity of the anti-biofouling light and a rotation speed of the propeller 61, wherein a higher light intensity is associated with a lower rotation speed. Also, it may be useful to have a higher light intensity after a period in which the system 10 has been off. In the context of a boat drive and steer assembly 6 which is equipped with an anti-biofouling system 10, it may furthermore be useful to have measures which are aimed at ensuring that when the propeller 61 is kept in a stationary condition for a certain period, the propeller 61 is made to rotate only for the purpose of achieving anti-biofouling effects on the surface 66 of the propeller 61, and not for the purpose of propulsion of the boat, so that the entire surface 66 of the propeller 61 may be kept clean from biofouling instead of only those portions of the surface 66 which happen to have a position for receiving most of the anti-biofouling light in the stationary condition. For example, in such a case, the propeller 61 may be rotated a predetermined number of times per day, while the anti-biofouling system 10 is on. In doing so, it may be advantageous to take care that at the end of the rotation cyclus, the propeller 61 is in another position about the rotation axis 62 than at the start of the rotation cyclus. In general, the boat drive and steer assembly 6 may be equipped with a suitable type of controller, which is programmed to realize control of the anti-biofouling system 10 as desired, by switching the system 10 on and off and setting the intensity of the anti-biofouling light, for example, and possibly also to take care that the propeller 61 is rotated from time to time when the propeller 61 appears to be in a stationary condition.

As explained in the foregoing, when the invention is applied, total coverage or near-total coverage of the surfaces 21, 22, 23, 24, 28, 52, 56, 66, 67, 68, 69, 72, 73, 74, 75, 76 to be kept clean from biofouling is realized, which should be understood such as to imply that at least 70% of the surfaces 21, 22, 23, 24, 28, 52, 56, 66, 67, 68, 69, 72, 73, 74, 75, 76 is covered by the anti-biofouling system 10, preferably at least 80% of the surfaces 21, 22, 23, 24, 28, 52, 56, 66, 67, 68, 69, 72, 73, 74, 75, 76 and even more preferably at least 90% of the surfaces 21, 22, 23, 24, 28, 52, 56, 66, 67, 68, 69, 72, 73, 74, 75, 76 and that it may even be possible to realize a situation in which 100% of the surfaces 21, 22, 23, 24, 28, 52, 56, 66, 67, 68, 69, 72, 73, 74, 75, 76 is covered by the anti-biofouling system 10.

The invention can be summarized as follows. A device 1, 2, 3, 4, 5, 6, 100 has surfaces 21, 22, 23, 24, 28, 52, 56, 66, 67, 68, 69, 72, 73, 74, 75, 76 and an anti-biofouling system 10 comprising at least one anti-biofouling light source 11, 12, 18, 19 for performing an anti-biofouling action on at least a majority of the surfaces 21, 22, 23, 24, 28, 52, 56, 66, 67, 68, 69, 72, 73, 74, 75, 76, the at least one anti-biofouling light source 11, 12, 18, 19 being adapted to emit rays of anti-biofouling light. In feasible practical embodiments of the device 1, 2, 3, 4, 5, 6, 100 according to the invention, the at least one anti-biofouling light source 11, 12, 18, 19 is arranged outside of the surfaces 21, 22, 23, 24, 28, 52, 56, 66, 67, 68, 69, 72, 73, 74, 75, 76, that is to say, is not integrated in at least one of the surfaces 21, 22, 23, 24, 28, 52, 56, 66, 67, 68, 69, 72, 73, 74, 75, 76 nor arranged directly on at least one of the surfaces 21, 22, 23, 24, 28, 52, 56, 66, 67, 68, 69, 72, 73, 74, 75, 76. The surfaces 21, 22, 23, 24, 28, 52, 56, 66, 67, 68, 69, 72, 73, 74, 75, 76 are configured relative to each other and to the at least one anti-biofouling light source 11, 12, 18, 19 such that during operation of the at least one anti-biofouling light source 11, 12, 18, 19, at least a majority of the surfaces 21, 22, 23, 24, 28, 52, 56, 66, 67, 68, 69, 72, 73, 74, 75, 76 is free from shadow with respect to the rays of anti-biofouling light from the at least one anti-biofouling light source 11, 12, 18, 19. Optionally, the surfaces 21, 22, 23, 24, 28, 52, 56, 66, 67, 68, 69, 72, 73, 74, 75, 76 are configured relative to each other and to the at least one anti-biofouling light source 11, 12, 18, 19 such that during operation of the at least one anti-biofouling light source 11, 12, 18, 19, the rays of anti-biofouling light emitted by the at least one anti-biofouling light source 11, 12, 18, 19 are allowed to reach the surfaces 21, 22, 23, 24, 28, 52, 56, 66, 67, 68, 69, 72, 73, 74, 75, 76 by impacting on the surfaces 21, 22, 23, 24, 28, 52, 56, 66, 67, 68, 69, 72, 73, 74, 75, 76 at a certain angle and/or skimming along the surfaces 21, 22, 23, 24, 28, 52, 56, 66, 67, 68, 69, 72, 73, 74, 75, 76.

The invention claimed is:

1. A device with an anti-biofouling system comprising:
at least one functional element, the at least one functional element having at least one functional surface,
wherein the system comprises at least one anti-biofouling light source, wherein the at least one anti-biofouling light source is arranged to emit rays of anti-biofouling light,
wherein the least one functional surface is configured relative to the at least one anti-biofouling light source such that during operation of the at least one anti-biofouling light source, at least a majority of the at least one functional surface is free from shadow with respect to the rays of anti-biofouling light,
wherein the at least one anti-biofouling light source is arranged to perform an anti-biofouling action on the at least one functional surface,
wherein the at least one functional element comprises one or more pipes,
wherein the one or more pipes have having a rectangular cross-section,
wherein the anti-biofouling system further comprises elongated anti-biofouling light sources extending perpendicular to the one or more pipes.

2. The device according to claim 1, wherein at the least one functional surface is configured for allowing the rays of anti-biofouling light to skim along the at least one functional surface.

3. The device according to claim 1,
wherein the at least one functional surface is a planar surface,
wherein the planar surface is oriented substantially parallel to and arranged alongside of a plane of the rays of anti-biofouling light.

4. The device according to claim 1,
wherein a majority of the at least one functional surface has a normal,
wherein the normal is at an angle of at most 90° towards at least one anti-biofouling light source.

5. The device according to claim 1, further comprising an enclosure,
wherein the enclosure is arranged to accommodate the at least one anti biofouling light source,
wherein the enclosure is arranged to accommodate a fluid,
wherein the at least one anti-biofouling light source is arranged to perform an anti-biofouling action on an interior surface of the enclosure.

6. The device according to claim 1, further comprising an enclosure,
wherein the enclosure is arranged to accommodate the at least one functional element,
wherein the enclosure is arranged to accommodate the at least one anti-biofouling light source,
wherein the at least one anti-biofouling light source is arranged to perform an anti-biofouling action on an interior surface of the enclosure.

7. A device with an anti-biofouling system comprising:
at least one functional element, the at least one functional element having at least one functional surface,
wherein the system comprises at least one anti-biofouling light source, wherein the at least one anti-biofouling light source is arranged to emit rays of anti-biofouling light,
wherein the least one functional surface is configured relative to the at least one anti-biofouling light source such that during operation of the at least one anti-biofouling light source, at least a majority of the at least one functional surface is free from shadow with respect to the rays of anti-biofouling light,
wherein the at least one anti-biofouling light source is arranged to perform an anti-biofouling action on the at least one functional surface,
wherein the at least one functional element is part of a heat exchanger system,
wherein the at least one functional element comprises a number of interconnected units in a successive arrangement,
wherein the interconnected units have an interior space,
wherein the interconnected units have at least one inlet,
wherein the at least one inlet is arranged to supply fluid to the interior space,
wherein the interconnected units have at least one outlet,
wherein the at least one outlet is arranged to discharge fluid from the interior space,
wherein the at least one anti-biofouling light source extends through the interconnected units.

8. The device according to claim 7,
wherein the heat exchanger system comprises corrugated sheets,
wherein the corrugated sheets are arranged to delimit the interconnected units,
wherein the corrugations of the sheets extend in a straight direction along an imaginary plane,
wherein the imaginary plane includes a longitudinal axis of at least one of the anti-biofouling light sources.

9. A device with an anti-biofouling system comprising:
at least one functional element, the at least one functional element having at least one functional surface,
wherein the system comprises at least one anti-biofouling light source, wherein the at least one anti-biofouling light source is arranged to emit rays of anti-biofouling light,
wherein the least one functional surface is configured relative to the at least one anti-biofouling light source such that during operation of the at least one anti-biofouling light source, at least a majority of the at least one functional surface is free from shadow with respect to the rays of anti-biofouling light, wherein the at least one anti-biofouling light source is arranged to perform an anti-biofouling action on the at least one functional surface,
wherein the device is a boat drive and steer assembly,
wherein the boat drive and steer assembly comprises a rotatable propeller and a fin extending downwardly from a propeller shaft casing,
wherein the propeller shaft casing serves to accommodate a shaft of the propeller and associated gearing,
wherein the at least one anti-biofouling light source is arranged in the boat drive and steer assembly at a position for realizing near-total coverage of the surface of the propeller as the propeller rotates
wherein the propeller shaft is hollow,
wherein a transparent material is applied in the propeller shaft,
wherein the transparent material is transparent to the rays of anti-biofouling light,
wherein the anti-biofouling system comprises an elongated light source,
wherein the elongated light source is arranged so as to extend through the hollow propeller shaft.

10. The device according to claim 1, further comprising an enclosure,
wherein the enclosure is arranged to accommodate the at least one anti-biofouling light source,
wherein the enclosure is arranged to accommodate the at least one element,
wherein the at least one anti-biofouling light source is arranged to perform an anti-biofouling action on an interior surface of the enclosure.

* * * * *